United States Patent [19]

Kablaoui et al.

[11] 3,950,385

[45] Apr. 13, 1976

[54] PREPARATION OF NITRONITRATES

[75] Inventors: Mahmoud Kablaoui, Wappingers Falls; Richard F. Love, Fishkill, both of N.Y.

[73] Assignee: Texaco Inc., New York, N.Y.

[22] Filed: Nov. 1, 1974

[21] Appl. No.: 519,901

[52] U.S. Cl. ................................. 260/466; 260/467
[51] Int. Cl.² ...................................... C07C 77/04
[58] Field of Search ........................... 260/466, 467

[56] References Cited
UNITED STATES PATENTS 3,192,248   6/1965   Bonetti et al. ..................... 260/467

FOREIGN PATENTS OR APPLICATIONS 1,078,045   8/1967   United Kingdom ................. 260/467

*Primary Examiner*—Leland A. Sebastian
*Attorney, Agent, or Firm*—T. H. Whaley; C. G. Ries; George J. Darsa

[57] ABSTRACT

A method for preparing vicinal nitronitrates by simultaneously contacting an alkene with oxygen and dinitrogen tetroxide in the presence of concentrated sulfuric acid. The nitronitrates so formed are useful as fuel additives as well as intermediates in the preparation of surfactants, fuel and lubricant additives, insecticides, fungicides, pharmaceuticals and polymers.

11 Claims, No Drawings

PREPARATION OF NITRONITRATES

BACKGROUND OF THE INVENTION

This invention relates to a method for preparing nitronitrates. In particular, this invention relates to a method of preparing nitronitrates from alkenes by means of a one-step nitrooxidation reaction.

Vicinal nitronitrates can be formed along with other nitration products by the action of dinitrogen tetroxide and oxygen on olefins. The reaction is free radical in nature and forms a complex mixture of products including low yields of nitronitrates, that is less than 50 percent, along with nitroalcohols, dinitro compounds and nitroolefins. Separation of the products is complicated by their instability to distillation. A more convenient method for the preparation of vicinal nitronitrates in higher yields is described in U.S. Pat. No. 3,282,983 which entails olefin nitrooxidation at low temperatures to form the intermediate nitroperoxy nitrate and the subsequent reduction of the intermediate with, for example, nitric oxide. While the art has produced the desired nitronitrates, the procedure employing two stages consequently gives rise to economic penalties and decreases the commercial attractiveness of the process.

It is therefore an object of this invention to provide a direct method for the preparation of nitronitrates.

It is another object of this invention to provide a method for the preparation of nitronitrates from alkenes by a single-step nitroxidation reaction.

Yet another object of this invention is to provide a method for the preparation of nitronitrates in good yields.

Other objects and advantages will become apparent from a reading of the following detailed description and examples.

SUMMARY OF THE INVENTION

Broadly, this invention contemplates a method of preparing nitronitrates which comprises contacting an alkene, dinitrogen tetroxide, oxygen and concentrated sulfuric acid.

The formation of nitronitrates by nitrooxidation in the presence of sulfuric acid is best suited to relatively less reactive alkenes. The alkenes employed as starting material in the instant method have at least 8 carbons in a chain and correspond to the formula:

$$R - CH = CH - R^1$$

where R and $R^1$ are hydrogen or alkyl groups of from 1 to 20 carbon atoms and where the sum of R and $R^1$ equals at least 6 carbon atoms and up to 24 carbon atoms or where R and $R^1$ together form a polymethylene radical of from 6 to 22 carbons or a substituted polymethylene radical of 6 to 22 carbons containing one or more alkyl groups. Alkenes contemplated herein and corresponding to the formula are illustrated by 1-,2-,3- and 4-octene, 1-,2-,3-,4- and 5-decene, 2-dodecene, 4-tetradecene, 1-hexadecene, 7-heptadecene, 10-eicosene, cyclooctene, cyclodecene, 4-pentylcyclotetradecene, cyclooctadecene, cycloeicosene and cyclodocosene. Mixtures of alkenes or cycloalkenes are similarly contemplated. More reactive alkenes possessing carbon chains of less than 8 carbons, such as trimethylpentene-1 and cyclohexene, afford only a complex mixture of products when employed as reactants in the instant method.

The preparation of the nitronitrates by the instant method from the designated alkenes or cycloalkenes is accomplished by simultaneously contacting a mixture of the alkene of the formula and concentrated sulfuric acid, that is 95 to 98 percent sulfuric acid, with dinitrogen tetroxide and oxygen at a temperature of between about -10° and 20°C., preferably between about 0° and 10°C. Temperatures in excess of 20°C. are undesirable because of the extensive amount of side reactions which occur leading to lower yields and increased difficulties in purifying the nitronitrate product and temperatures below -10°C. require excessive refrigeration thereby rendering the process economically unattractive.

The mole ratios of the individual components in the instant invention provides the method with high yields of nitronitrates. In particular, the mole ratio of alkene to dinitrogen tetroxide to oxygen in the single step nitrooxidation reaction can vary between about 1:1:1 and 1:2:100, preferably between about 1:1.3:10 and 1:1.5:20. Further, it is essential that the mole ratio of alkene to sulfuric acid during the nitrooxidation reaction be between about 1:1 and 5:1, preferably between 2:1 and 4:1. The ratio of alkene to sulfuric acid is critical to the instant method inasmuch as ratios greater and less than that set forth cause substantial diminution in the yield of the nitronitrate and additionally complex product mixtures are formed including nitroalcohols, dinitro compounds, nitroketones and nitronitroso compounds. Further, the acid employed is concentrated (95–98%) sulfuric acid as the presence of or addition of water during the reaction results in a reduced yield and selectivity to the nitronitrate. Also, the use of other acids, such as phosphoric, nitric or trifluoroacetic acid, in place of sulfuric acid have been found to result in a complex mixture of products.

The reaction is conveniently undertaken by preparing a solution of the alkene and sulfuric acid to which is introduced dinitrogen tetroxide and oxygen. Generally dinitrogen tetroxide and oxygen are respectively introduced into the reaction system at a rate of between about 10 and 25 mg/min/gram alkene and between about 20 and 120 ml/min/gm of alkene. The reaction time is normally between about one-quarter and one hour although longer and shorter periods may be employed.

The conversion of the alkene by the instant method to the corresponding nitronitrate can be undertaken, if desired, in the presence of an inert diluent. The diluent facilitates the contact between the reactants and in general we employ those inert liquid diluents having a boiling point of between about 30° and 100°C. such as n-hexane, isohexane, n-heptane, carbon tetrachloride, benzene and petroleum ether.

It will be understood that the dinitrogen tetroxide employed is actually an equilibrium mixture of dinitrogen tetroxide and nitrogen dioxide with the equilibrium being driven to essentially 100 percent dinitrogen tetroxide at 0°C. and essentially 100 percent nitrogen dioxide at 140°C. at 1 atmosphere pressure. The term dinitrogen tetroxide as used herein denotes the equilibrium mixtures as well as pure $N_2O_4$ compound. The oxygen employed in the instant invention may be in pure form or as a mixture, e.g., air or in admixture with inert gases such as nitrogen or argon.

In the practice of the instant invention, the alkene of the formula is nitrooxidized with dinitrogen tetroxide, oxygen and sulfuric acid at the temperatures recited, suitably in an inert diluent, under the conditions and mole ratios set forth above thereby providing a reaction product rich in nitronitrates of the formula:

where R and R$^1$ are as heretofore defined. In the reaction, the particular olefinic carbon to which the nitro and nitrate groups respectively attach is a random choice of the reaction when R and R$^1$ are alkyl or together form a polymethylene radical. In the formula above, when for example R$^1$ is hydrogen, the nitro group forms on the terminal olefinic carbon with the nitrate group on the olefinic carbon adjacent thereto.

Specific examples of the nitronitrates formed by the method of this invention are illustrated by 1-nitro-2-octyl nitrate, 1-nitro-2-decyl nitrate, mixture of 4-nitro-5-tetradecyl nitrate and 5-nitro-4-tetradecyl nitrate, 1-nitro-2-hexadecyl nitrate, 1-nitro-2-cyclooctyl nitrate and 1-nitro-2-cyclodecyl nitrate.

The method described herein provides as the reaction product a material rich in nitronitrates and as a co-product of the reaction, the corresponding nitroalcohol. Small amounts of other materials, usually less than about 10 percent, may in some instances be formed such as corresponding nitroketones or carboxylic acids.

At the completion of the reaction, the nitronitrate may be recovered by water dilution and extraction of the organic portion with ether. Solvent removal affords a nitronitrate rich product. Further, purification can be accomplished by passing a solution of the nitronitrate, such as a 60/40 mixture of isohexane/methylene chloride, through silica gel which retains the major impurity, a nitroalcohol. When the product contains small amounts of nitroalcohol, generally less than 10 percent, slurrying the solution with silica gel is usually sufficient to effect nitroalcohol removal.

The nitronitrates formed pursuant to the instant method are useful as fuel additives. They are also useful as intermediates in the preparation of surfactants, fuel and lubricant additives, insecticides, fungicides, pharmaceuticals and polymers.

In order to more fully illustrate the nature of our invention and the manner of practicing the same, the following examples are presented.

EXAMPLE I

A solution of 9.8 grams (50 mmoles) of tetradecene-1 in 75 milliliters of carbon tetrachloride containing 1 milliliter (20 mmoles) of concentrated sulfuric acid was nitrooxidized with 6.0 grams (65 mmoles) of N$_2$O$_4$ and 19 grams (595 mmoles) of oxygen at 5°C. over a period of one-half hour. Upon completion of the reaction, the mixture was diluted with water and ether, and the organic phase was separated, dried and stripped. The residue weighing 14.5 grams (98 percent yield) was identified by infrared spectroscopy and nuclear magnetic resonance to contain 90 parts by weight (86 percent yield) of 1-nitro-2-tetradecyl nitrate and 9 parts (10 percent yield) of 1-nitro-2-tetradecanol.

EXAMPLE II

Following the procedure of Example I, 9.8 grams (50 mmoles) of tetradecene-1 in 75 milliliters of carbon tetrachloride were reacted with one milliliter (20 mmoles) of concentrated sulfuric acid, 6.9 grams (75 mmoles) of N$_2$O$_4$ and 21.6 grams (675 mmoles) of oxygen at 5°C. over a period of 45 minutes. At the completion of the reaction, the organic fraction isolated (16 grams) was found to contain 76.5 parts (80 percent yield) of 1-nitro-2-tetradecyl nitrate, 6 parts (7.5 percent yield) of 1-nitro-2-tetradecanol and 0.5 parts carboxylic acids and unstripped solvent.

EXAMPLE III

Following the procedure of Example I, 9.8 grams (50 mmoles) of tetradecene-1, 75 milliliters of carbon tetrachloride, 3 milliliters (60 mmoles) of concentrated sulfuric acid were contacted with 4.6 grams (50 mmoles) of N$_2$O$_4$ and 14 grams (440 mmoles) of oxygen at 5°C. over a 30 minute period. Upon work-up and analysis, the reaction product (13.8 grams) was found to consist of 42 parts of 1-nitro-2-tetrdecyl nitrate, 49 parts of 1-nitro-2-tetradecanol and the remainder a mixture of nitroolefin and carboxylic acids.

EXAMPLE IV

Employing the procedure of the previous examples, 9.8 grams (50 mmoles) of tetradecene-1 in 75 milliliters of carbon tetrachloride containing 0.5 milliliter (10 mmole) of concentrated sulfuric acid was reacted with 4.6 grams (50 mmoles) of N$_2$O$_4$ and 14 grams of oxygen at about 5°C. After isolating the product (12.6 grams), it was found to contain 38 parts (30 percent yield) of 1-nitro-2-tetradecyl nitrate, 52 parts (49 percent yield) of 1-nitro-2-tetradecanol and 7 parts (6.8 percent yield) of 1-nitro-2-tetradecanone.

EXAMPLE V

A mixture of 9.8 grams of tetradecene-1, 75 milliliters of carbon tetrachloride and 1 milliliter of concentrated sulfuric acid was contacted with 4.6 grams (50 mmoles) of N$_2$O$_4$ and 14 grams of oxygen at about 5°C. Upon work-up and isolation, the product (13.6 grams) was found to consist of 81 parts (73 percent yield) of 1-nitro-2-tetradecyl nitrate and 19 parts (20 percent yield) of 1-nitro-2-tetradecanol.

EXAMPLE VI

A solution of 5.6 grams (50 mmoles) of 2,4,4-trimethylpentene-1 in 75 milliliters of carbon tetrachloride containing 1.0 milliliter (20 mmoles) of concentrated sulfuric acid was contacted with 4.6 grams (50 mmoles) of N$_2$O$_4$ and 14 grams of oxygen (440 mmoles) at 5°C. as in the previous examples. Upon work-up and isolation, there was obtained 8.0 grams of product which was found to be 31 parts (23 percent yield) of nitronitrate, 34 parts (30 percent yield) of nitroalcohol, 33 parts (27 percent yield) of dinitrotrimethylpentene, and 3 parts of a trinitro substituted material.

EXAMPLE VII

A solution of 5.5 grams (50 mmoles) of cyclooctene in 75 milliliters of carbon tetrachloride containing 1 milliliter (20 mmoles) of concentrated sulfuric acid was contacted with 6.9 grams (75 mmoles) of N$_2$O$_4$ and 21.6 grams (675 mmoles) of oxygen at 5°C. over a period of 45 minutes. Upon dissolution in water, ether extraction and product concentration, there was obtained 10.3 grams of product which was found by analysis to contain 79 parts (75 percent yield) of 2-nitrocyclooctyl nitrate and 18 parts (20 percent yield) of 2-nitrocyclooctanol.

Employing the same procedure, 5.5 grams of cyclooctene in 75 milliliters of benzene containing 1 milliliter of concentrated sulfuric acid was contacted with 6.5 grams of $N_2O_4$ and 21 grams of oxygen at 10°C. Upon concentration of the product (9.7 grams), analysis found it to contain 72 parts (64 percent yield) of 2-nitrocyclooctyl nitrate and 24 parts (25 percent yield) of 2-nitrocyclooctanol.

EXAMPLE VIII

A solution of 4.4 grams (50 mmoles) of cyclohexane in 50 milliliters of carbon tetrachloride containing 1 milliliter of concentrated sulfuric acid was treated with 6.9 grams of $N_2O_4$ and 21 grams of oxygen at about 5°C. Analysis of the isolated product (7.3 grams) showed it consisted of a mixture of 2-nitrocyclohexyl nitrate (30 percent yield), 2-nitrocyclohexanol, nitrocyclohexane and carboxylic acids.

EXAMPLE IX

A solution of 11.2 grams (50 mmoles) of hexadecene-1 in 75 milliliters of isohexane containing 1 milliliter (20 mmole) of concentrated sulfuric acid was treated with 4.6 grams of $N_2O_4$ and 14 grams of oxygen at about 5°C. Analysis of the isolated product found it to consist of 65 parts (49 percent yield) of 1-nitro-2-tetradecyl nitrate and 30 parts (26 percent yield) of 1-nitro-2-tetradecanol.

EXAMPLE X

A solution of 9.8 grams of tetradecene-1 in 75 milliliters of carbon tetrachloride containing 1 milliliter (21 mmoles) of 90 percent nitric acid was treated with 4.6 grams of $N_2O_4$ and oxygen under the conditions used in Example V. Upon isolation, the reaction product was found by analysis to contain a complex mixture of nitronitrate, nitroalcohol, nitronitroso- and dinitro- compounds, and where the nitronitrate constituted less than 50 percent of the mixture.

EXAMPLE XI

Example X was repeated except that 1 milliliter (16 mmoles) of $H_3PO_4$ was employed in place of nitric acid. The isolated product (12.7 grams) upon analysis was found to consist of 73 parts (64 percent yield) of 1,2-dinitretetradecane and about 20 parts (19.5 percent yield) of 1-nitro-2-tetradecanol. Less than 1 part of nitronitrate was detected.

EXAMPLE XII

Example X was repeated except that 1 milliliter (15 mmoles) of trifluoroacetic acid was employed in place of nitric acid. The isolated product (15.5 grams) upon analysis was found to be a mixture of primarily 1,2-dinitrotetradecane along with some nitronitrosotetradecane, and lesser amounts of nitroalcohol and nitronitrate.

We claim:
1. A method of preparing nitronitrates which comprises contacting an alkene, dinitrogen tetroxide, oxygen and concentrated sulfuric acid.
2. A method according to claim 1 wherein the mole ratio of said alkene to sulfuric acid is between about 1:1 and 5:1.
3. A method according to claim 1 wherein the mole ratio of said alkene to sulfuric acid is between 2:1 and 4:1.
4. A method according to claim 1 wherein said contacting is at a temperature of between about -10° and 20°C.
5. A method according to claim 1 wherein said contacting is at a temperature between about 0° and 10°C.
6. A method according to claim 1 wherein said alkene has at least 8 carbon atoms in a chain.
7. A method according to claim 1 the mole ratio of said alkene to dinitrogen tetroxide to oxygen is between about 1:1:1 and 1:2:100.
8. A method according to claim 1 the mole ratio of said alkene to dinitrogen tetroxide to oxygen is between about 1:1.3:10 and 1:1.5:20.
9. A method according to claim 1 wherein said alkene is tetradecene-1.
10. A method according to claim 1 wherein said alkene is hexadecene-1.
11. A method according to claim 1 wherein said alkene is cyclooctene.

* * * * *